US00PP16978P2

(12) United States Plant Patent
Kawashima

(10) Patent No.: US PP16,978 P2
(45) Date of Patent: Aug. 8, 2006

(54) ***OSTEOSPERMUM* PLANT NAMED 'KAKEGAWA AU17'**

(50) Latin Name: *Osteospermum fruticosum*
Varietal Denomination: Kakegawa AU17

(75) Inventor: Moriya Kawashima, Matsumoto (JP)

(73) Assignee: Sakata Seed Corporation, Yokohama (JP)

( * ) Notice: Subject to any disclaimer, the term of this patent is extended or adjusted under 35 U.S.C. 154(b) by 8 days.

(21) Appl. No.: 11/054,766

(22) Filed: Feb. 10, 2005

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
(74) *Attorney, Agent, or Firm*—Jondle & Associates P.C.

(57) ABSTRACT

An *Osteospermum* cultivar particularly distinguished by its white inflorescence color, basal branching, and compact growth habit is disclosed.

1 Drawing Sheet

Genus and species: *Osteospermum fruticosum.*
Variety denomination: 'Kakegawa AU17'.

BACKGROUND OF THE NEW PLANT

'Kakegawa AU17' originated from a gene pool population made in Misato, Japan. In May 1999, three *Osteospermum* varieties were intercrossed and $F_1$ seed from this cross was bulked to make the population. The three *Osteospermum* varieties used in the intercross were 'Pink Passion' (unpatented, now only available in 'Passion Mix'), an unnamed *Osteospermum* breeding line of unknown origin (unpatented) with white inflorescences and day-neutral blooming and an unnamed *Osteospermum* line (unpatented) with white inflorescences. It is unknown which two lines are the parents.

$F_1$ seed was sown in the greenhouse in April 2000. Plants were later transplanted outdoors for evaluation in Misato, Japan. Criteria for selection included compact growth habit, basal branching and white inflorescence color. In August 2000, one single-plant selection was made based on the above criteria and vegetatively propagated. The selection subsequently was named 'Kakegawa AU17' and found to reproduce true to type in successive generations of asexual propagation.

DESCRIPTION OF PHOTOGRAPHS

This new *Osteospermum* plant is illustrated by the accompanying photographs which show the plant's form, foliage and inflorescences. The colors shown are as true as can be reasonably obtained by conventional photographic procedures.

DESCRIPTION OF THE NEW CULTIVAR

Figure 1:
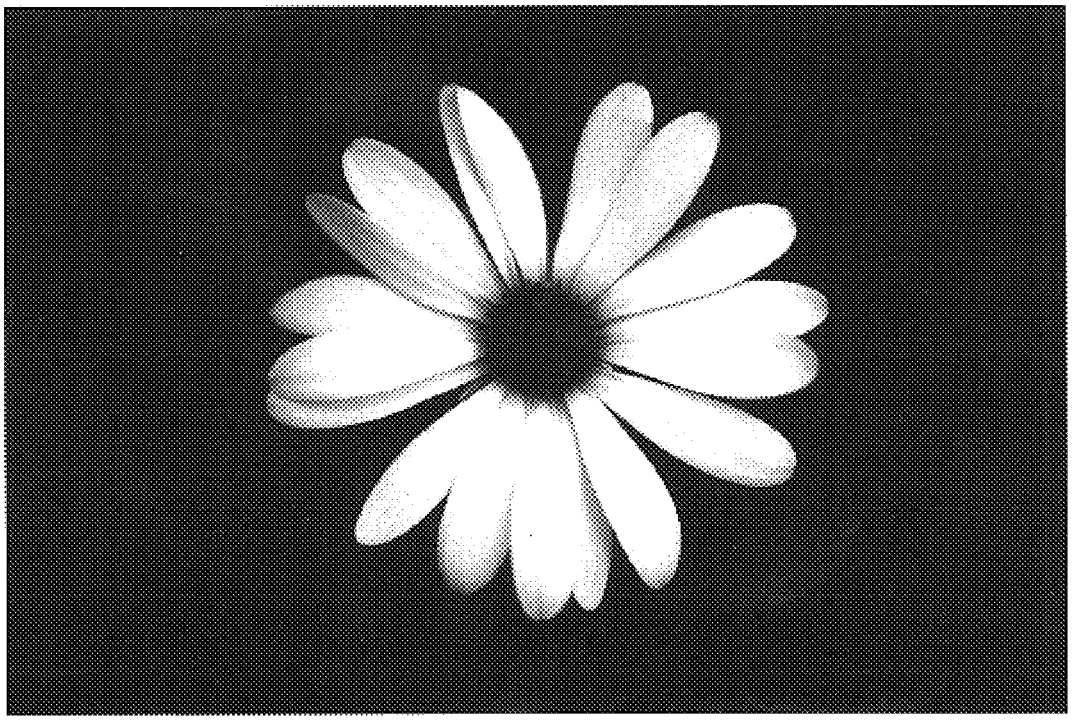
FIG. 1 shows the mature inflorescence.
Figure 2:
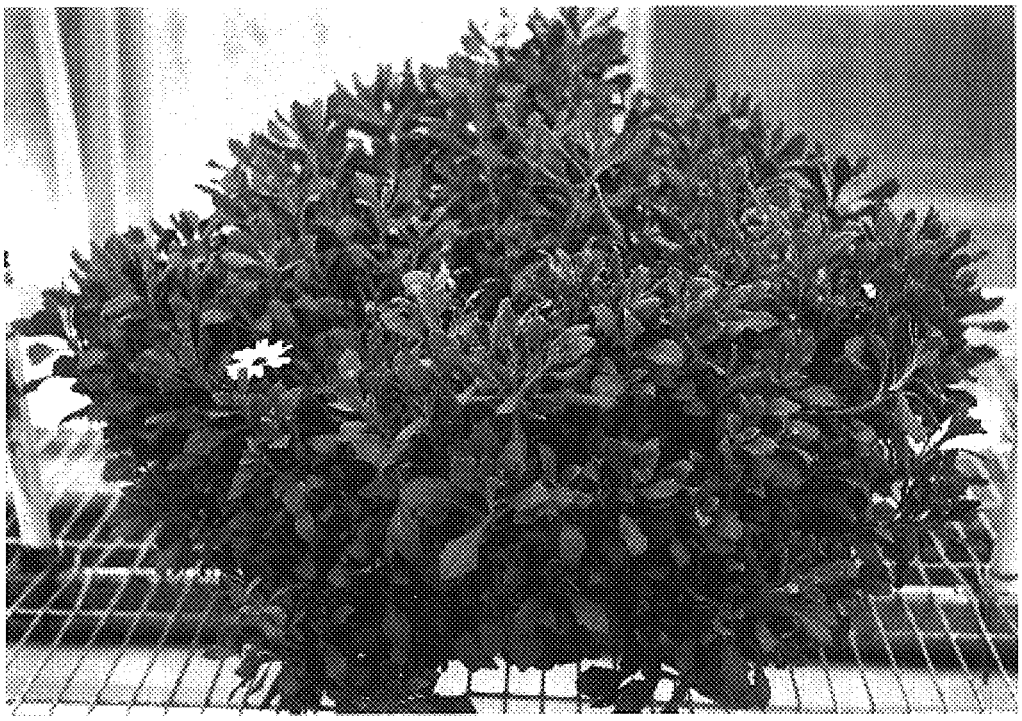
FIG. 2 shows overall plant habit.

The following detailed descriptions set forth the distinctive characteristics of 'Kakegawa AU17'. The data which define these characteristics were collected from asexual reproductions carried out in Salinas, Calif. Data was collected on plants grown approximately four months from transplanting rooted cuttings into 6-inch pots under greenhouse conditions in Salinas, Calif. Color references are to The R.H.S. Colour Chart of The Royal Horticultural Society of London (R.H.S.).

DESCRIPTION OF THE NEW PLANT

Classification:
*Family.*—Compositae.
*Botanical.*—*Osteospermum fruticosum.*

Parentage:
*Female parent.*—Unknown.
*Male parent.*—Unknown.

Growth:
*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of DIP 'N GROW root-inducing solution in water. The trays are misted hourly during rooting.
*Environmental conditions for plant growth.*—Rooted cuttings are transplanted to pots with a 16 cm diameter, one plant per pot. Peat-based growing media is used. The pots are watered using a 150–200 ppm fertilizer solution containing 18% nitrogen, 8% phosphorus and 18% potassium. The soil is allowed to dry between waterings. During the first few weeks after transplanting, the plants were grown under evening temperatures around 15–18° C. for good root growth. When plants reached 7.5–10 cm in height, they were pinched back to 5–6 leaves to promote branching. Spring and summer daytime high temperatures in Salinas, Calif., where the data was collected, range from 16–25° C.
*Time to bloom from propagation.*—Approximately four weeks when rooted vegetative cuttings are transferred to a 16 cm. diameter pot. Flowering season is all year in the United States. Vernalization is not required to induce flowering.

Plant description:
*Habit.*—Upright.
*Life cycle.*—Perennial.
*Form.*—Highly branching.

*Height.*—40 cm.
*Width.*—65 cm.

Stems:
*Internode length.*—1.5–2.0 cm.
*Stem description.*—Ancipital, woody at soil line.
*Stem diameter.*—0.5–0.6 cm.
*Stem color.*—RHS 144B (yellow-green).
*Pubescence.*—Slight.
*Pubescence shape.*—Linear.
*Pubescence color.*—RHS 155A (white).

Leaves:
*Arrangement.*—Alternate.
*Shape.*—Oblanceolate.
*Apex.*—Mucronate.
*Base.*—Decurrent.
*Margin.*—Serrate.
*Venation.*—Pinnate.
*Surface.*—Dull, smooth.
*Surface pubescence.*—Slight.
*Length.*—4.0–4.5 cm.
*Width.*—2.5 cm.
*Thickness.*—0.1 cm.
*Color.*—Upper surface: RHS 137A (green). Lower surface: RHS 137C (green).
*Venation color.*—Upper surface: RHS 143B (green). Lower surface: RHS 143B (green).
*Petiole length.*—4.1–5.1 cm.
*Petiole diameter.*—0.2 cm.
*Petiole color.*—RHS 144A (yellow-green).

Inflorescence:
*Type.*—Capitulum (head); disc florets are perfect and ray florets are carpellate.
*Flowering habit.*—Determinate.
*Lastingness of inflorescences.*—3–4 days on the plant.
*Fragrance.*—None.
*Seed production.*—None observed.
*Diameter.*—6 cm.
*Depth.*—1.5 cm.
*Ray floret number.*—18 per inflorescence.
*Disc diameter.*—1.0–1.2 cm.
*Disc floret number.*—80.
*Peduncle length.*—6.0–7.0 cm.
*Peduncle diameter.*—0.2 cm.
*Peduncle color.*—RHS 144A (yellow-green).
*Peduncle texture.*—Dull, slight pubescence.
*Phyllaries.*—Number, arrangement: About 18 in a single whorl per inflorescence; free, arranged symmetrically. Length: 0.9–1.2 cm. Width: 0.1 cm. Apex: Mucronate. Base: Cuneate. Margin: Entire. Shape: Lanceolate. Color: Upper surface: RHS 143A (green). Lower surface: RHS 143A (green).

Ray florets (ligules):
*Corolla.*—One ray per ray floret; only the outer row of florets is the ray florets.
*Ray floret length.*—3 cm.
*Ray floret width.*—0.6–0.8 cm.
*Ray floret shape.*—Spatulate.
*Ray floret apex.*—Mucronate.
*Ray floret margin.*—Entire.
*Ray floret color.*—Upper surface: Majority (upper 2.8 cm) of petal is RHS 155A (white); base portion at the junction with the peduncle is RHS 77B (purple). Lower surface: Edge is RHS 155A (white); main portion is RHS 82B (purple-violet) with two RHS 77C (purple) outer stripes and two RHS 77A (purple) inner stripes.
*Ray floret pubescence.*—Glabrous.
*Ovary.*—Superior.
*Pistil form.*—One style with two stigma branches.
*Pistil length.*—0.3–0.4 cm.
*Stigma color.*—RHS 92A (violet-blue).
*Style color.*—RHS 83A (violet).

Disc florets:
*Disc floret color.*—Upper surface: RHS N77A (purple). Lower surface: RHS N155A (white).
*Disc floret shape.*—Ensiform.
*Disc floret apex.*—Acute.
*Disc floret base.*—Cuneate.
*Disc floret surface.*—Dull, pubescent.
*Disc floret margin.*—Entire.
*Disc floret size.*—Length: 0.4 cm. Width: 0.1 cm.
*Pistil form.*—One style with two stigma branches.
*Ovary.*—Superior.
*Style color.*—RHS 163A (yellow-orange).
*Stigma color.*—RHS 92A (violet-blue).
*Stamens.*—5, fused into a single tube.
*Location of gynoecium.*—Ray florets and disc florets.
*Anther color.*—Translucent.
*Pollen color.*—RHS 25D (orange).
*Location of androecium.*—Disc florets.

Disease and insect resistance: Very disease resistant, however, plants are susceptible to aphids, thrips, whiteflies and worms.

COMPARISON WITH KNOWN CULTIVARS

'Kakegawa AU17' is a distinct variety of *Osteospermum* owing to its white inflorescence color, basal branching and compact growth habit. 'Kakegawa AU17' is most similar to the *Osteospermum* variety named 'Wildside' (U.S. Plant Pat. No. 10,603); however, there are differences as described in the table below:

TABLE 1

| Characteristic | 'Kakegawa AU17' | 'Wildside' |
|---|---|---|
| Ray floret (ligule) color, upper | Majority (upper 2.8 cm) of ray floret is RHS 155A (white); base portion (junction with peduncle) is RHS 77B (purple) | 71A (red-purple) at maturity |
| Basal branching | Present | None |
| Growth habit | Upright | Broad |

I claim:

1. A new and distinct cultivar of *Osteospermum* plant as shown and described herein.

* * * * *